United States Patent [19]
Khattar et al.

[11] Patent Number: 5,859,267
[45] Date of Patent: Jan. 12, 1999

[54] PROCESS FOR IMPROVING COLOR OF BASIC METAL ORGANIC SALTS AND STABILIZING HALOGEN-CONTAINING POLYMERS THEREWITH

[75] Inventors: Rajesh Khattar, Richmond Heights; Benjamin Paul Labovitz, Cleveland Heights, both of Ohio

[73] Assignee: OMG Americas, Inc., Cleveland, Ohio

[21] Appl. No.: 744,642

[22] Filed: Nov. 6, 1996

Related U.S. Application Data

[60] Provisional application No. 60/006,384, Nov. 8, 1995 and provisional application No. 60/019,719, Jun. 13, 1996.

[51] Int. Cl.$^6$ .............................. C07C 51/50; C07C 27/26
[52] U.S. Cl. ................................................ 554/4; 568/702
[58] Field of Search ................................... 554/4; 568/702

[56] References Cited

U.S. PATENT DOCUMENTS

| | | | |
|---|---|---|---|
| 2,626,904 | 11/1953 | Asseff et al. | 260/399 |
| 2,760,970 | 8/1956 | Le Suer | 260/429 |
| 2,767,164 | 10/1956 | Asseff et al. | 260/139 |
| 2,798,852 | 7/1957 | Wiese et al. | 252/42.7 |
| 2,802,816 | 8/1957 | Asseff et al. | 260/139 |
| 2,971,014 | 2/1961 | Mastin | 260/398 |
| 2,989,463 | 6/1961 | Mastin | 252/25 |
| 3,027,325 | 3/1962 | McMillen et al. | 252/33 |
| 3,031,284 | 4/1962 | Andress | 44/76 |
| 3,147,232 | 9/1964 | Norman et al. | 260/23 |
| 3,194,823 | 7/1965 | Le Suer et al. | 260/414 |
| 3,342,733 | 9/1967 | Robbins et al. | 252/33 |
| 3,533,975 | 10/1970 | Scullin | 260/23 |
| 3,773,664 | 11/1973 | Le Suer | 252/40.7 |
| 3,779,922 | 12/1973 | Le Suer | 252/34.7 |
| 4,159,973 | 7/1979 | Hoch et al. | 260/23 X |
| 4,252,698 | 2/1981 | Ito et al. | 260/18 EP |
| 4,665,117 | 5/1987 | Quinn | 524/327 |

*Primary Examiner*—Paul J. Killos
*Attorney, Agent, or Firm*—Wood, Herron & Evans, L.L.P.

[57] ABSTRACT

A light colored basic alkali or alkaline earth metal organic salt is obtained by the reaction of a basic metal compound, an alkyl phenol and/or a carboxylic acid, carbon dioxide, and thereafter post-treating the reaction product with an organic phosphite. Alkaline earth metal salts of phenols and carboxylic acids include barium or calcium. Organic phosphites include trialkyl or dialkyl phosphites such as triisodecyl phosphite or diisooctyl phosphite.

28 Claims, No Drawings

PROCESS FOR IMPROVING COLOR OF BASIC METAL ORGANIC SALTS AND STABILIZING HALOGEN-CONTAINING POLYMERS THEREWITH

RELATED APPLICATIONS

This application is a continuation of Provisional Applications Ser. Nos. 60/006,384, filed on Nov. 8, 1995, and 60/019,719, filed on Jun. 13, 1996, both of which are incorporated herein in their entireties by reference.

FIELD OF THE INVENTION

The present invention relates to a process for producing light colored hydrocarbon-soluble basic alkali and alkaline earth metal salts of phenols and/or monocarboxylic acids where phenols are used as promoters. More particularly, the invention concerns a process for producing light colored basic alkaline earth metal organic salts by reacting a basic alkaline earth metal compound, an alkyl phenol and/or a carboxylic acid, and carbon dioxide, to form a reaction product and thereafter post-treating the reaction product with an organic phosphite to improve color. The basic alkaline earth metal organic salts of the present invention are used as stabilizers for halogen-containing polymers such as polyvinyl chloride (PVC).

BACKGROUND OF THE INVENTION

The preparation of overbased calcium or barium salts of carboxylic acids, alkyl phenols, and sulfonic acids are disclosed in the following U.S. Pat. Nos. 2,616,904; 2,760,970; 2,767,164; 2,798,852; 2,802,816; 3,027,325; 3,031,284; 3,342,733; 3,533,975; 3,773,664; and 3,779,922. The use of these overbased metal salts in the halogen-containing organic polymer is described in the following U.S. Pat. Nos. 4,159,973; 4,252,698; and 3,194,823. The use of overbased barium salt in stabilizer formulations has increased during recent years. This is due, in the main, to the fact that overbased barium salts possess performance advantages over the neutral barium salts. The performance advantages associated with overbased barium salts are low plate-out, excellent color hold, good long-term heat stability performance, good compatibility with the stabilizer components, etc. Unfortunately, most of the overbased barium salts are dark in color and, while these dark colored overbased barium salts are effective stabilizers for halogen-containing organic polymer, their dark color results in the discoloration of the end product. This feature essentially prohibits the use of dark colored overbased barium salts in applications where a light colored polymer product is desired.

According to the teachings of U.S. Pat. No. 4,665,117, light colored alkali or alkaline earth metal salts are prepared where alkyl phenol is used as a promoter. However, alkyl phenol is also a major cause for the development of color in the final product. This problem is overcome by the use of propylene oxide which displaces the hydrogen of the phenolic hydroxyl group and thereby restricts the formation of colored species. However, there are disadvantages associated with this approach, principally due to the toxic nature of propylene oxide. Propylene oxide is classified as a possible carcinogen and laboratory animal inhalation studies have shown evidence of a link to cancer. Propylene oxide is also listed as a severe eye irritant, and prolonged exposure to propylene oxide vapors may result in permanent damage to the eye. Furthermore, propylene oxide is extremely flammable and explosive in nature under certain conditions. Propylene oxide boils at 94° F. and flashes at −20° F. As a result, extreme precautions are required to handle propylene oxide at the plant site. Special storage equipment is required for propylene oxide and other safety features are necessary. U.S. Pat. No. 4,665,117 describes the use of propylene oxide at 150° C. At this temperature, propylene oxide will be in the gaseous phase. Under these operating conditions, more than stoichiometric amounts of propylene oxide are required to carry the reaction to completion because propylene oxide will escape from the reaction mixture and this requires additional handling of the excess propylene oxide.

Accordingly, there is a need for further improvements in making basic metal salts and for overcoming the problems associated with the use of propylene oxide in producing a light colored liquid basic alkaline earth metal organic salt for use in stabilizing vinyl halide polymers and other halogen-containing polymers.

SUMMARY OF THE INVENTION

The present invention relates to a process for improving the color of a basic alkaline earth metal organic salt prepared from mixtures containing a phenol. For example, the process involves reacting a basic alkaline earth metal compound, an alkyl phenol and/or a carboxylic acid, and carbon dioxide, to produce a basic metal organic salt and a color-producing component which is a phenol or phenolic reaction product. Thereafter, the basic metal salt reaction product is treated with an organic phosphite to react with the color-producing component and thereby improve its color.

The organic phosphites suitable for use include various diorganic phosphites and triorganic phosphites. Depending upon the specific organic phosphite and the color-producing component, the color improving reaction may proceed in different ways, as developed more particularly hereinafter. For instance, in one method of the invention, the organic phosphite is believed to destroy the colored species produced by or in conjunction with the phenol. In another form of the method, the organic phosphite is believed to prevent the formation of the colored species by reaction with the phenol. While not wishing to be bound by theory or mechanism, it is considered highly unexpected in such a complex basic metal salt reaction mixture for the organic phosphite to react with the color-producing phenol or phenol reaction product and thereby provide a light colored basic metal organic salt. This is so notwithstanding the known use of organic phosphites in stabilizer compositions for vinyl halide resins.

There are a number of benefits associated with the inventive process over the prior art methods. Organic phosphites are easier and safer to handle than propylene oxide. The organic phosphites are high boiling and high flash compounds, while propylene oxide is a low boiling and highly combustible material. Preferably, organic phosphites used in this invention are liquid and can be very easily introduced into the reaction system. Also, stoichiometric amounts of phosphite may be used to carry out the reaction. This is in contrast to the use of propylene oxide where in practice an excess of propylene oxide is needed to carry out a reaction because of the gaseous state of propylene oxide. Moreover, phosphite-treated basic metal organic salts obtained by the invention exhibit performance advantages over the products disclosed in U.S. Pat. No. 4,665,117 such as better compatibility in stabilizer systems and lower viscosities to thereby allow easy handling, storage and filtration.

DESCRIPTION OF THE PREFERRED EMBODIMENTS

A. The Basic Process and Critical Features

The process of the present invention for improving the color and stability of basic alkali or alkaline earth metal salts obtained from mixtures containing a phenol comprises the steps of (A) preparing, in the absence of free oxygen, a mixture comprising at least one alkaline earth metal base, at least one alkyl phenol, the ratio of the equivalents of said alkaline earth metal base to the alkyl phenol being greater than 1:1; or, a mixture comprising at least one alkaline earth metal base, at least one phenol, at least one monocarboxylic acid, and optionally at least one aliphatic alcohol, the ratio of equivalents of monocarboxylic acid to phenol being at least about 1.1:1, and the ratio of equivalents of the metal base to the combination of the other components being greater than 1:1, (B) treating said mixture with an acidic gas in the absence of free oxygen until the titratable basicity (phenolphthalein indicator) of the mixture has been substantially reduced, and (C) treating the reaction mixture containing the basic metal organic salt with an organic phosphite which reacts with the color-producing component present in the final mixture. It is preferred that the entire process involving steps (A), (B) and (C) be conducted in the absence of free oxygen since the presence of oxygen or oxidizing agents results in more highly colored product. Generally, the process is conducted in an atmosphere of nitrogen.

The most critical features of the method include step (C) wherein the basic metal organic salt which is produced as an intermediate or reaction product at the conclusion of step (B) is treated with an organic phosphite capable of inhibiting and/or destroying the color-producing component or product which is generated by the phenol or phenolic reaction product in the above-described reaction. If the color-producing component is not inhibited and/or destroyed in accordance with the method of the present invention, the product obtained by the process is darker in color and, on standing, continues to darken in color. When the process of the present invention is followed, the initial product is light in color and does not appreciably darken on standing. Acceptable color by ASTM D1500 standard is up is to about 3, preferably about 1 to 2.

As stated above, while not desiring to be bound by theory or mechanism, depending upon the color-producing component and organic phosphite, the color improving reaction may proceed in different ways. For example, where phenol is present, a trialkyl phosphite such as triisodecyl phosphite may react with the phenol by substitution of phosphorous for the hydrogen of the phenol and form a bond with oxygen which has more stability than the hydrogen-oxygen bond, thereby preventing the phenol from forming color species in the reaction mixture. As another example, where the phenol has reacted to form a phenolic reaction product which is a color-producing component such as a quinone, then a diisooctyl phosphite may destroy the phenolic reaction product to improve color. In either case, the organic phosphite improves the color by either inhibiting or destroying color-producing components attributable to phenol or phenolic reaction products.

B. Basic Metal Organic Salts

Throughout this specification and claims, the term "basic" as applied to the alkali or alkaline earth metal organic salts is used to refer to metal compositions wherein the ratio of total metal contained therein to the organic moieties is greater than the stoichiometric ratio of the neutral metal salt. That is, the number of metal equivalents is greater than the number of equivalents of the organic moiety. In some instances, the degree to which excess metal is found in the basic metal salt is described in terms of a "metal ratio". Metal ratio as used herein indicates the ratio of total of alkaline earth metal in the oil-soluble composition to the number of equivalents of the organic moiety. The basic metal salts often have been referred to in the art as "overbased" or superbased" to indicate the presence of an excess of the basic component.

The process of the present invention may be used to prepare lighter colored basic salts of phenates and/or carboxylates. For example, when basic alkaline earth metal salts of alkyl phenols and carboxylates are desired, the mixture utilized in step (A) comprises at least one alkaline earth metal base, and at least one phenol, at least one monocarboxylic acid, and optionally at least one aliphatic alcohol, the ratio of equivalents of monocarboxylic acid to phenol being at least about 1.1:1, and the ratio of equivalents of the metal base to the combination of the other components being greater than 1:1. The mixtures utilized in step (A) of the process of the present invention are prepared and maintained in the absence of free oxygen. An atmosphere of nitrogen is preferred.

The alkali or alkaline earth metal bases utilized as component and may be derived from any of the alkali or alkaline earth metals. Metal bases derived from alkaline earth metals are preferred and of these, the calcium and barium bases are particularly preferred. The metal bases include the metal oxides and hydroxides, and in some instances, the sulfides, hydrosulfides, etc. The alkyl phenol reactant may be derived from phenol itself or from naphthol, or from other polynuclear phenolic compounds. It may also be a bisphenol such as is obtained from the condensation of an aldehyde or ketone with a phenol. The alkyl phenols may contain one or more alkyl groups on the aromatic nucleus, and it is necessary that the number of carbon atoms in the alkyl groups be sufficient to yield oil-soluble overbased metal phenates. In addition to the alkaline earth metal base and the phenol, the mixture may also contain at least one monocarboxylic acid. The monocarboxylic acids may be aliphatic or aromatic monocarboxylic acids or mixtures thereof. Among the aliphatic monocarboxylic acids which can be utilized in the present invention are the aliphatic monocarboxylic acids containing an average of at least about 6 carbon atoms and more generally an average of from about 6 to about 30 carbon atoms. The mixture useful in step (A) optionally may contain at least one aliphatic alcohol which serves as a promoter in the overall process. The alcohols which are useful as promoters include any one of the various available substituted or unsubstituted aliphatic or cycloaliphatic alcohols containing from 1 to about 20 or more carbon atoms. The amount of the phenol and optionally the alcohol included in the mixture as a promoter is not critical. The promoters are included in the mixture to contribute to the utilization of the acidic gas during treatment of the mixture with the acidic gas. Generally, at least about 0.1 equivalent and preferably from about 0.05 to about 10 equivalents of the phenol (and the alcohol if present) per equivalent of a monocarboxylic is employed. Larger amounts, for example, up to about 20 to about 25 equivalents of alcohol and/or phenol may be used, especially in the case of lower molecular weight alcohols and phenols. Water, which may optionally also be present in the mixture, may be present as water added as such to the mixture, or the water may be present as "wet alcohol", "wet" phenol, hydrates of the alkali or alkaline earth metal salts, or other type of chemically combined water with the metal salts.

In addition to the components described above, the reaction mixtures used to prepare the basic metal salts ordinarily will contain a diluent. Generally, any hydrocarbon diluent can be employed, and the choice of diluent is dependent in part on the intended use of the mixture. Most generally, the hydrocarbon diluent will be a non-volatile diluent such as the various natural and synthetic oils of lubricating viscosity.

The amount of basic alkali or alkaline earth metal base utilized in the preparation of basic phenates is an amount which is more than one equivalent of the base per equivalent of phenol, and more generally, with be an amount sufficient to provide at least three equivalents of the metal base per equivalent of alkyl phenol. Larger amounts can be utilized to form more basic compounds, and the amount of metal base included may be any amount up to that amount which is no longer effective to increase the proportion of metal in the product. When preparing the mixture, the amount of phenol and the optional alcohol included in the mixture is not critical except that the ratio of equivalents of monocarboxylic acid to phenol should be at least about 1.1:1; that is, the monocarboxylic acid is present in excess with respect to the phenol. The ratio of equivalents of the metal base of the combination of the other components in mixture should be greater than 1:1 in order to provide a basic product. More generally, the ratio of equivalents will be at least 3:1.

The step of the process (B) involves treating the mixtures described above with an acidic gas in the absence of free oxygen until the titratable basicity is determined using a phenolphthalein. Generally, the titratable basicity is reduced to a base number below about 10. The first two steps of the process of the present invention require no unusual operating conditions other than preferably the exclusion of free oxygen. The ingredients in step (A) are mixed, generally heated and then treated with the acidic gas, and the mixture may be heated to a temperature which is sufficient to drive off some of the water contained in the mixture. The treatment of the mixture with the acidic gas preferably is conducted at elevated temperatures, and the range of temperatures used for this step may be any temperature above ambient temperature up to about 200° C., and more preferably from a temperature of about 75° C. to about 200° C. Higher temperatures may be used such as 250° C., but there is no apparent advantage in the use of such higher temperatures. Ordinarily, a temperature of about 150° C. is satisfactory. By the term "acidic gas" as used in this specification and in the claims is meant a gas which upon reaction with water will produce an acid. Thus, such gases as sulfur dioxide, sulfur trioxide, carbon dioxide, carbon disulfide, hydrogen sulfide, etc., are exemplary of the acidic gases which are useful in the process of this invention. Of these acids, sulfur dioxide and carbon dioxide are preferred, and the most preferred is carbon dioxide.

Procedures for preparing basic alkali and alkaline earth metal salts of alkyl phenols and/or carboxylates involving steps (A) and (B) of the present invention are well know in the art, and it is not believed necessary to unduly lengthen the specification with additional description of the procedures. The procedures known in the art can be utilized and preferably are conducted in the absence of free oxygen. Examples of patents which describe the preparation of basic metal phenates include, for example, U.S. Pat. Nos. 2,989,463 and 2,971,014, the specifications of which are hereby incorporated by reference. The preparation of the basic metal salts of monocarboxylic acids utilizing (B) also is well know and different procedures have been described in the prior art such as in U.S. Pat. Nos. 3,194,823 and 3,147,232, the disclosures of which are hereby incorporated by reference. U.S. Pat. No. 4,665,117 is also incorporated herein by reference.

C. Organic Phosphites

The third and critical step in the process of the present invention involves (C) treating the reaction mixture with at least one organic phosphite which is capable of reducing, inhibiting, and/or eliminating the color-producing component of phenol or phenolic reaction during the above-described process in steps (A) and (B).

Preferably, the composition or reaction product obtained in step (B) is post-treated with at least one organic phosphite. Without limitation, the organic phosphites may be generally characterized by the formula

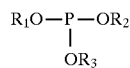

in which $R_1$, $R_2$ and $R_3$ are hydrogen, alkyl, alkenyl, aryl, alkaryl, aralkyl and cycloalkyl radicals or groups, and substituted derivatives thereof. Thus, triphosphites and diphosphites are suitable including trialkyl or dialkyl phosphites, for example, having from about 1 to 18 carbon atoms. Specific examples of organic phosphites, including the preferred liquid organic phosphites, are tributyl phosphite, triisooctyl phosphite and triisodecyl phosphite, diisooctyl phosphite, dibutyl phosphite and tetrakis isodecyl 4,4-isopropylidene diphosphite, diphenyl isodecyl phosphite, phenyl neopentylene glycol phosphite, diphenyl phosphite, triphenyl phosphite, phenyl diisodecyl phosphite and poly (dipropyleneglycol phenyl phosphite. Other organic phosphites may be used in view of this description and exemplification.

The amounts of the organic phosphites suitable for use in the treatment are sufficient to inhibit or destroy the color-producing body. More specifically, a molar ratio of phenol to organic phosphite should be between about 0.5–2:1 in order to substantially completely inhibit or destroy the color-producing body.

As developed above, these organic phosphites are easier and safer to handle than most prior art expedients, such as propylene oxide. The organic phosphites are high boiling and high flash compounds, while propylene oxide is a low boiling and highly combustible material. The organic phosphites used in this invention are preferably liquid and can be very easily introduced into the reaction system in contrast to the propylene oxide approach where excess of propylene oxide is needed to carry out a reaction because of the gaseous state of propylene oxide.

D. Halogen-Containing Polymer

A halogen-containing polymer, such as a vinyl halide resin, most commonly stabilized with the basic metal salts of this invention is polyvinyl chloride. It is to be understood, however, that this invention is not limited to a particular vinyl halide resin such as polyvinyl chloride or its copolymers. Other halogen-containing resins which are employed and which illustrate the principles of this invention include chlorinated polyethylene, chlorosulfonated polyethylene, chlorinated polyvinyl chloride, and other vinyl halide resin types. Vinyl halide resin, as understood herein, and as appreciated in the art, is a common term and is adopted to define those resins or polymers usually derived by polymerization or copolymerization of vinyl monomers including vinyl chloride with or without other comonomers such as ethylene, propylene, vinyl acetate, vinyl ethers, vinylidene chloride, methacrylate, acrylates, styrene, etc. A simple case is the conversion of vinyl chloride $H_2C{=}CHCl$ to polyvinyl chloride $(CH_2CHCl{-})_n$ wherein the halogen is bonded to the carbon atoms of the carbon chain of the polymer. Other examples of such vinyl halide resins would include vinylidene chloride polymers, vinyl chloride-vinyl ester copolymers, vinyl chloride-vinyl ether copolymers, vinyl chloride-vinylidene copolymers, vinyl chloride-propylene copolymers, chlorinated polyethylene, and the like. Of course, the vinyl halide commonly used in the industry is the chloride, although others such as bromide and fluoride may be used. Examples of the latter polymers include polyvinyl bromide, polyvinyl fluoride, and copolymers thereof.

Heavy metal compound heat stabilizers of vinyl halide resin compositions are well known. These metal compounds serve to capture HCI liberated during heat processing of the vinyl halide resin composition into its final shape. The heavy metal can be lead, cadmium, barium or antimony, for example. The stabilizers are usually metal salts of a carboxylic acid, advantageously of a $C_8$–$C_{24}$ carbon chain link monocarboxylic acid such as lauric, oleic, stearic, octoic, or similar fatty acid salts. Mixed metal salts of such acids, and their preparation, are familiar to those skilled in the art to which this present invention pertains. Mixed metallic carboxylates involving calcium/zinc or barium/zinc blends alone and in combination with other stabilizers such as beta-diketones, phosphite salts and phenolic antioxidants have been used. The metal stabilizer is a mixed metal salt of a carboxylate acid. Mixed metal salts of such acids, and their preparation, are also familiar to those skilled in the art to which this present invention pertains.

The following examples illustrate the preparation of the basic alkaline earth metal organic salts in accordance with the method of the present invention, but these examples are not considered to be limiting the scope of this invention. Unless otherwise indicated in the following examples and elsewhere in the specification and claims, all parts and percentages are by weight, and all temperatures are in degrees centigrade.

EXAMPLE 1

A mixture of 165 parts of commercially available mixture of aliphatic alcohols containing 12 to 18 carbon atoms, 141 parts of is nonylphenol and 600 parts of mineral oil is prepared and purged with nitrogen to remove any oxygen present in the system. The nitrogen purge is maintained throughout the entire process. After a period of 20 minutes, the mixture is heated while stirring to a temperature of from about 90° C. to about 98° C. At this temperature, 1200 parts of barium hydroxide monohydrate are added incrementally over a 30-minute period and the temperature of the mixture is then increased to about 150°–155° C., while removing any water which is driven off during the heating. Oleic acid (258 parts) is then added over a 30–40 minute period while again removing the water of reaction which comes over. After all of the oleic acid is added, the mixture is treated with carbon dioxide at a rate of about 2 SCFH for approximately 4 hours to reduce the titratable basicity of the mixture to about 8.

The carbon dioxide feed is then stopped while maintaining the nitrogen purge for an additional 30 minutes to dry the mixture. The mixture is then filtered hot (about 125° C.) with a filter aid. The filtrate is a dark colored liquid product which was then treated with diphenyl phosphite (215 parts) and stirred at room temperature for 20–30 minutes. This results in the formation of a light colored barium organic liquid which is the desired product with a barium content of 34%. The ASTM color is found to be less than 1.5.

EXAMPLE 2

The procedures of Example 1 were repeated, except that diisooctyl phosphite (256 parts) was substituted for diphenyl phosphite in the post-treatment phase of the process which resulted in essentially the same ASTM color (D1500) of less than 1.5 for the product.

EXAMPLE 3

A mixture of 165 parts of commercially available mixture of aliphatic alcohols containing 12 to 18 carbon atoms, 141 parts of nonylphenol and 600 parts of mineral oil is prepared and purged with nitrogen to remove any oxygen present in the system. The nitrogen purge is maintained throughout the entire process. After a period of 20 minutes, the mixture is heated while stirring to a temperature of from about 90° C. to about 98° C. At this temperature, 1200 parts of barium hydroxide monohydrate are added incrementally over a 30-minute period and the temperature of the mixture is then increased to about 150°–155° C., while removing any water which is driven off during the heating. Oleic acid (258 parts) is then added over a 30–40 minuted period while again removing the water of reaction which comes over. After all of the oleic acid is added, the mixture is treated with carbon dioxide at a rate of about 2 SCFJ for approximately 4 hours to reduce the titratable basicity of the mixture to about 8.

The carbon dioxide feed is then stopped while maintaining the nitrogen purge for an additional 30 minutes to dry the mixture. The mixture was then cooled to 115°–120° C. Triisodecyl phosphite (TDP) (320 parts) was then added to the reaction mixture. The reaction mixture was then heated at 115°–120° C. for 8–10 hours. It was then filtered hot (115°–120° C.) with a filter aid, and the filtrate is a desired product with a barium content of 34%. The ASTM color (D1500) is found to be 1.

EXAMPLE 4

The procedures of Example 3 were repeated except that tributyl phosphite (170 parts) was substituted for triisodecyl phosphite in the post-treatment phase of the example and the ASTM color (1500) is found to be 1.

EXAMPLE 5

In order to demonstrate the heat-stabilizing effectiveness of the basic alkaline earth metal organic salt of this invention, the triisodecyl phosphite treated product of Example 3 was formulated as a stabilizer for PVC and designated hereinafter "STABILIZER A", as follows:

| STABILIZER A | Percent by Weight |
| --- | --- |
| Example 3 w/TDP (34% Overbased) | 25 |
| 22% Zinc Octoate | 6.8 |
| Diphenyl isodecyl phosphite | 42.4 |
| Dibenzoyl methane | 2.5 |
| Bisphenol A | 2 |
| Oleic acid | 2 |
| Benzoic acid | 2 |
| Hydrocarbon Solvent | 17.3 |

A presently available 28% overbased barium dodecyl phenate, sold by Lubrizol 2106 was also formulated and designated "STABILIZER B", as follows:

| STABILIZER B | Percent by Weight |
| --- | --- |
| Lubrizol 2106 (28% Overbased Barium dodecyl phenate) | 30.4 |

-continued

| STABILIZER B | Percent by Weight |
| --- | --- |
| 22% Zinc Octoate | 6.8 |
| Diphenyl isodecyl phosphite | 42.4 |
| Dibenzoyl methane | 2.5 |
| Bisphenol A | 2 |
| Oleic acid | 2 |
| Benzoic acid | 2 |
| Hydrocarbon Solvent | 11.9 |

STABILIZER A and STABILIZER B were each formulated in a standard polyvinyl chloride formulation at a level of 2.5 parts where the balance of the formulation included 100 parts of polyvinyl chloride (Geon 100×450), 30 parts dioctylphthalate, 3 parts epoxidized soybean oil, 9 parts titanium dioxide, 10 parts calcium carbonate and 0.15 parts stearic acid. The PVC formulation was milled at 350° F. for 5 minutes and static heat stability was determined at 375° F. Over a period of about 68 minutes, STABILIZER A of this invention demonstrated an improved heat stabilizing effectiveness in comparison to STABILIZER B as measured by color change. Accordingly, the basic alkaline earth metal organic salts of this invention which had been post-treated with organic phosphites may be substituted for currently available basic metal salts with improved performance in color as measured by a calorimeter as an indication of yellowing. A detail of the color values obtained by STABILIZERS A and B are shown by the following table.

| | COLOR B VALUES* | |
| --- | --- | --- |
| Time (min) | STABILIZER A | STABILIZER B |
| 7.5 | 7.45 | 7.74 |
| 15 | 9.07 | 9.83 |
| 22.5 | 12.12 | 13.31 |
| 30 | 18.08 | 20.49 |
| 37.5 | 18.65 | 20.76 |
| 45 | 19.4 | 22.25 |
| 52.5 | 21.32 | 22.99 |
| 60 | 22.07 | 22.89 |
| 68 | 22.49 | 23.05 |

*These color B values were determined by ASTM E313-73

The above description provides a disclosure of particular embodiments of the invention and is not intended for the purpose of limiting the same thereto. As such, the invention is not limited to only the above described embodiments. Rather, it is recognized that one skilled in the art would understand alternative embodiments in view of the above description that fall within the scope of the invention.

What is claimed is:

1. A process for improving the color of a basic alkali or alkaline earth metal organic salt prepared from mixtures containing a phenol consisting essentially of:

preparing a reaction mixture containing a basic alkali or alkaline earth organic metal salt and a color-producing component selected from the group consisting of a phenol and a phenolic reaction product and, treating the reaction mixture with an organic phosphite in an amount sufficient to react with the color-producing component and thereby improve the color of said basic alkali or alkaline earth metal organic salt.

2. The process of claim 1 wherein said organic phosphite has an organic radical selected from the group consisting of alkyl, alkenyl, aryl, alkylaryl, arylalkyl, cycloalkyl, and substituted derivatives thereof.

3. The process of claim 1 wherein said organic phosphite is a trialkyl phosphite.

4. The process of claim 3 wherein said phosphite has an alkyl group having from 1 to 18 carbon atoms.

5. The process of claim 3 wherein said phosphite is selected from the group consisting of tributyl phosphite, triisooctyl phosphite and triisodecyl phosphite.

6. The process of claim 1 wherein said phosphite is a dialkyl phosphite.

7. The process of claim 6 wherein said phosphite is selected from the group consisting of diisooctyl phosphite, dibutyl phosphite and tetrakis isodecyl 4,4-isopropylidene diphosphite.

8. The process of claim 1 wherein said phosphite is selected from the group of a diphenyl isodecyl phosphite, phenyl neopentylene glycol phosphite, diphenyl phosphite, triphenyl phosphite, phenyl diisodecyl phosphite and poly (dipropyleneglycol) phenyl phosphite.

9. The method of claim 1 wherein said organic phosphite is a liquid organic phosphite.

10. The method of claim 1 wherein the amount of said phosphite is sufficient to react with substantially all of the color-producing component present.

11. The process of claim 1 wherein the metal is an alkaline earth metal.

12. The process of claim 11 wherein the alkaline earth metal is calcium or barium.

13. The process of claim 1 wherein the reaction mixture is prepared from a mixture of an alkali or alkaline earth metal base, a phenol, and optionally a monocarboxylic acid or an aliphatic alcohol, and the process comprises the further step of first treating the reaction mixture with carbon dioxide in the absence of free oxygen until the titratable basicity of the mixture has been substantially reduced and then treating the reaction mixture with the organic phosphite.

14. The method of claim 13 wherein said alkaline earth metal is calcium or barium and the organic phosphite is selected from the group consisting of dialkyl phosphite and trialkyl phosphite.

15. The method of claim 14 wherein said phosphite is selected from the group consisting of tributyl phosphite, triisooctyl phosphite and triisodecyl phosphite.

16. The method of claim 14 wherein said phosphite is selected from the group consisting of diisooctyl phosphite and diphenyl phosphite.

17. A stabilizer composition prepared in accordance with the process of claim 1.

18. A stabilizer composition prepared in accordance with the process of claim 2.

19. A stabilizer composition prepared in accordance with the process of claim 4.

20. A stabilizer composition prepared in accordance with the process of claim 12.

21. A stabilizer composition prepared in accordance with the process of claim 13.

22. A stabilizer composition prepared in accordance with the process of claim 14.

23. A halogen-containing polymer composition comprising a halogen-containing polymer and a heat stabilizing amount of the composition of claim 17.

24. A halogen-containing polymer composition comprising a halogen-containing polymer and a heat stabilizing amount of the composition of claim 18.

25. A halogen-containing polymer composition comprising a halogen-containing polymer and a heat stabilizing amount of composition of claim 19.

26. A halogen-containing polymer composition comprising a halogen-containing polymer and a heat stabilizing amount of composition of claim 20.

27. A halogen-containing polymer composition comprising a halogen-containing polymer and a heat stabilizing amount of composition of claim 21.

28. A halogen-containing polymer composition comprising a halogen-containing polymer and a heat stabilizing amount of composition of claim 22.

* * * * *